United States Patent [19]

Bender et al.

[11] Patent Number: 5,693,795
[45] Date of Patent: Dec. 2, 1997

[54] PROCESS FOR THE MANUFACTURE OF 4H-IMIDAZO[1,5-A][1,4]BENZODIAZEPINES

[75] Inventors: Karl-Heinz Bender, Neuenburg; Manfred Breuninger, Bad Säckingen; Manfred Froom, Freiburg, all of Germany; Siegfried Schmitt, Reinach; Kurt Steiner, Starrkirch-Wil, both of Switzerland

[73] Assignee: Hoffmann-La Roche Inc., Nutley, N.J.

[21] Appl. No.: 724,801

[22] Filed: Oct. 2, 1996

[30]  Foreign Application Priority Data

Oct. 10, 1995 [CH] Switzerland ............................. 2854/95

[51] Int. Cl.$^6$ ................................................. C07D 487/04
[52] U.S. Cl. ................................................. 540/562
[58] Field of Search ........................................... 540/562

[56] References Cited

U.S. PATENT DOCUMENTS 4,280,957  7/1981  Walser et al. .
4,307,237  12/1981  Walser et al. .

Primary Examiner—Robert T. Bond
Attorney, Agent, or Firm—George W. Johnston; Ellen Ciambrone-Coletti; Robert A. Silverman

[57]  ABSTRACT

A process for the manufacture of 4H-imidazo[1,5-a][1,4]benzodiazepine derivatives of formula I

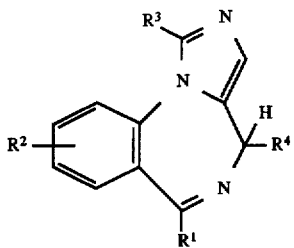

wherein
$R^1$ is phenyl or mono- or disubstituted phenyl;
$R^2$ is hydrogen, halogen, nitro, cyano, trifluoromethyl or lower alkyl;
$R^3$ is hydrogen or lower alkyl; and
$R^4$ is hydrogen or lower alkyl and of pharmaceutically usable salts of these compounds by decarboxylating a 4H-imidazo[1,5-a][1,4]benzodiazepinecarboxylic acid of formula II

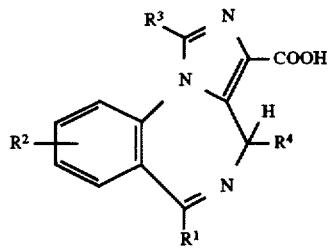

wherein
$R^1$, $R^2$, $R^3$ and $R^4$ have the above significances, at elevated temperature and under elevated pressure in the presence of an organic solvent. The compounds of formula I and their pharmaceutically usable acid addition salts are known muscle relaxants, sedatives and anticonvulsants.

13 Claims, No Drawings

PROCESS FOR THE MANUFACTURE OF 4H-IMIDAZO[1,5-A][1,4]BENZODIAZEPINES

FIELD

The invention relates to a process for the manufacture of 4H-imidazo[1,5-a][1,4]benzodiazepine derivatives of formula I

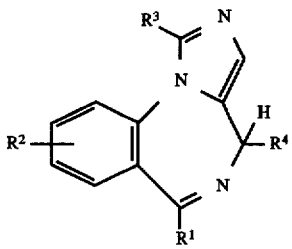

wherein $R^1$ is phenyl or mono- or disubstituted phenyl;
$R^2$ is hydrogen, halogen, nitro, cyano, trifluoromethyl or lower alkyl;
$R^3$ is hydrogen or lower alkyl; and
$R^4$ is hydrogen or lower alkyl and of pharmaceutically usable salts of these compounds.

BACKGROUND

U.S. Pat. No. 4,280,957, incorporated herein by reference, describes a process for the manufacture of imidazobenzodiazepine derivatives of formula I

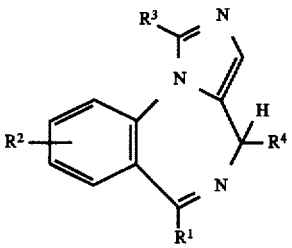

wherein $R^1$ is phenyl or mono- or disubstituted phenyl;
$R^2$ is hydrogen, halogen, nitro, cyano, trifluoromethyl or lower alkyl;
$R^3$ is hydrogen or lower alkyl; and
$R^4$ is hydrogen or lower alkyl and of pharmaceutically usable salts of these compounds.

The process described in U.S. Pat. No. 4,280,957 comprises decarboxylating the corresponding imidazobenzodiazepine-carboxylic acid at 100°-350° C., optionally in the presence of a solvent and a catalyst. This process has the disadvantage that in addition to the desired 4H-imidazo[1,5-a][1,4]-benzodiazepine derivative of formula I there is obtained a considerable amount of the corresponding isomeric 6H-imidazo[1,5-a][1,4]-benzodiazepine derivative, which requires an expensive re-isomerization.

SUMMARY OF THE INVENTION

The process in accordance with the invention comprises decarboxylating a 4H-imidazo[1,5-a][1,4]benzodiazepine-carboxylic acid of formula II

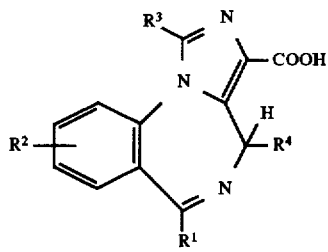

wherein $R^1$, $R^2$, $R^3$ and $R^4$ have the above significances, at elevated temperature and under elevated pressure in the presence of an organic solvent.

DETAILED DESCRIPTION OF THE INVENTION

The term "lower alkyl" embraces straight-chain or branched saturated hydrocarbon groups with up to 7 carbon atoms, such as methyl, ethyl, n-propyl, isopropyl, n-butyl, sec.butyl, isobutyl, n-pentyl, n-hexyl and the like.

The term "halogen" embraces chlorine, bromine, fluorine and iodine.

The phenyl group denoted by $R^1$ can be mono- or di-substituted. Suitable substituents embrace halogen and nitro, preferably in the 2-position of the phenyl ring. A fluorine substituent in the 2-position of the phenyl ring is preferred.

Optical isomerism occurs when $R^4$ signifies lower alkyl and not only optical antipodes but also the racemates are embraced by the present invention.

The term "pharmaceutically usable salt" embraces salts with inorganic and organic pharmaceutically usable acids such as hydrochloric acid, sulphuric acid, phosphoric acid, citric acid, formic acid, maleic acid, acetic acid, succinic acid, tartaric acid, p-toluenesulphonic acid and the like.

The decarboxylation can be conveniently effected in a temperature range of 150°-350° C., preferably at 250°-350° C. A temperature range of 280°-290° C. is especially preferred.

In accordance with the invention the decarboxylation is carried out under elevated pressure, conveniently in a pressure range of 50-150 bar, preferably at 90-110 bar.

The process can be carried out not only as a batch process but also as a continuous process. A continuous operation of the process is preferred.

n-Butanol, n-butyl acetate, ethyl acetate, ethanol, ethylene glycol, hexane, isopropyl acetate, n-propanol, tetralin and toluene are suitable solvents for the decarboxylation of the compounds of formula II in the scope of the present invention. n-Butanol is preferred.

The amount of solvent is not critical.

The crude product consists of the two isomeric derivatives 4H-imidazo[1,5-a][1,4]benzodiazepine and 6H-imidazo[1,5-a]-[1,4]benzodiazepine. The content of 4H-imidazo[1,5-a][1,4]-benzodiazepine derivative is approximately 85%.

The working up of the crude product can be effected by recrystallization from a suitable solvent. n-Butanol, butyl acetate, t.-butyl methyl ether, ethanol, ethyl acetate, isopropyl acetate and mixtures of these solvents are suitable solvents for the recrystallization. Isopropyl acetate is preferred. The desired 4H-imidazo[1,5-a][1,4]benzodiazepine derivative crystallizes out, while the more polar 6H-imidazo[1,5-a][1,4]benzodiazepine derivative remains in solution and can be separated.

If desired, the crystallizate can be purified further by repeated recrystallization, for example from ethanol.

The content of 6H-imidazo[1,5-a][1,4]benzodiazepine derivative is below 0.2% after the purification.

The mother liquors of the crystallizations can be concentrated, with a mixture of 4H-imidazo[1,5-a][1,4] benzodiazepine derivate and 6H-imidazo[1,5-a][1,4] benzodiazepine being obtained in an isomer ratio between 70:30 and 50:50. The isomer ratio can be influenced by adding KOH. This is conveniently carried out by suspending the crystal cake obtained from the mother liquor with solid KOH in a suitable solvent, for example in n-butanol, for at least 12 hours. The isomer ratio is then approximately 95:5. Further purification can be carried out by recrystallization as described above after separating the KOH.

The compounds of formula I and their pharmaceutically usable acid addition salts are known muscle relaxants, sedatives and anticonvulsants. The compounds of formula II are also known. (See U.S. Pat. No. 4,280,957).

The invention is illustrated in more detail in the following example of a continuous high-pressure decarboxylation of 8-chloro-6-(2-fluoro-phenyl)-1-methyl-4H-imidazo[1,5a][1,4]benzodiazepine-3-carboxylic acid.

EXAMPLE

Manufacture of 8-chloro-6-(2-fluoro-phenyl)-1-methyl-4H-imidazo[1,5a ][1,4]benzodiazepine.

The continuously performed process embraces the following steps:

a) Decarboxylation

8-Chloro-6-(2-fluoro-phenyl)-1-methyl-4H-imidazo[1,5a]-[1,4]benzodiazepine-3-carboxylic acid was added to the continuous reactor in the form of a 50% suspension in n-butanol. The decarboxylation was effected at approximately 280° C. and 100 bar. The residence time in the reactor is 2–4 minutes, with a conversion of above 99% being achieved. The product mixture consists of approximately 85% 8-chloro-6-(2-fluoro-phenyl)-1-methyl-4H-imidazo[1,5a][1,4]benzodiazepine and 15% 8-chloro-6-(2-fluoro-phenyl)-1-methyl-6H-imidazo[1,5a][1,4]benzodiazepine.

b) Working Up of the Crude Product

The n-butanol was evaporated to a content of approximately 10%.

Two-fold recrystallization from isopropyl acetate gives almost pure 8-chloro-6-(2-fluoro-phenyl)-1-methyl-4H-imidazo[1,5a][1,4]benzodiazepine. The 8-chloro-6-(2-fluoro-phenyl)-1-methyl-6H-imidazo[1,5a][1,4]benzodiazepine content lies below 0.2%.

c) Further Purification

The product was slightly yellow in colour and is recrystallised from ethanol.

The yield is 45–55% after working up the crude product and further purification.

d) Working-up of the Mother Liquors

The mother liquors of the crystallizations from isopropyl acetate and from ethanol were combined and concentrated. The mixture of 8-chloro-6-(2-fluoro-phenyl)-1-methyl-4H-imidazo[1,5a][1,4]benzodiazepine and 8-chloro-6-(2-fluoro-phenyl)-1-methyl-6H-imidazo[1,5a][1,4] benzodiazepine crystallized out almost quantitatively. The isomer ratio lied between 70:30 and 50:50. For re-isomerization, the isomer mixture was suspended at room temperature for at least 12 hours in n-butanol with the addition of solid KOH. Thereafter, the crystallizate was separated and digested several times in water until the KOH had been removed quantitatively from the crystallizate. The moist crystallizate, which now had an isomer ratio of approximately 95:5, was recrystallized twice from isopropyl acetate. Residual water was removed as an azeotrope. Further purification was effected by recrystallization from ethanol.

Yield 15–25%

We claim:

1. A process for the manufacture of 4H-imidazo[1,5-a][1,4]benzodiazepine derivatives of formula I

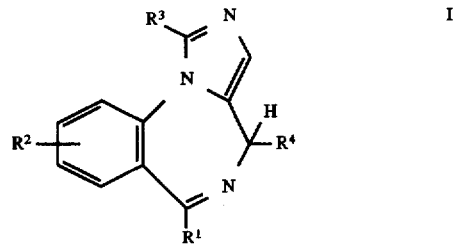

wherein $R^1$ is phenyl or mono- or disubstituted phenyl;

$R^2$ is hydrogen, halogen, nitro, cyano, trifluoromethyl or lower alkyl;

$R^3$ is hydrogen or lower alkyl; and $R^4$ is hydrogen or lower alkyl and of pharmaceutically usable salts of these compounds, which process comprises decarboxylating a 4H-imidazo[1,5-a][1,4]-benzodiazepinecarboxylic acid of formula II

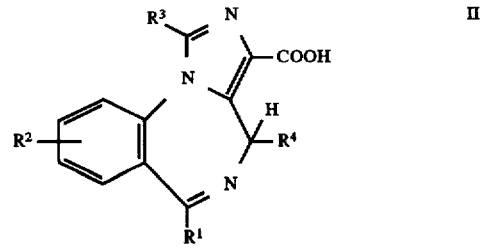

wherein $R^1$, $R^2$, $R^3$ and $R^4$ have the above significances, at elevated temperature and under elevated pressure in the presence of an organic solvent.

2. A process according to claim 1, wherein 8-chloro-6-(2-fluoro-phenyl)-1-methyl-4H-imidazo[1,5a][1,4]benzodiazepine is manufactured.

3. A process according to claim 1, wherein the decarboxylation is effected at a temperature of 150°–350° C.

4. A process according to claim 3, wherein the temperature is 250°–350° C.

5. A process according to claim 1, wherein the decarboxylation is effected at a pressure of 50–150 bar.

6. A process according to claim 5, wherein the pressure is 90–110 bar.

7. A process according to claim 1, wherein the decarboxylation is carried out in the presence of n-butanol, n-butyl acetate, ethyl acetate, ethanol, ethylene glycol, hexane, isopropyl acetate, n-propanol, tetralin or toluene.

8. A process according to claim 7, wherein the decarboxylation is carried out in n-butanol.

9. A process according to claim 1, which is carried out as a continuous process.

10. A process according to claim 1, wherein the product obtained is purified by recrystallization from n-butanol, butyl acetate, t-butyl methyl ether, ethanol, ethyl acetate or isopropyl acetate.

11. A process according to claim 10, wherein the recrystallization is effected from isopropyl acetate.

12. A process according to claim 10, wherein the product which is purified by recrystallization is further purified by repeated recrystallization.

13. A process according to claim 12, wherein the repeated recrystallization is effected from ethanol.

* * * * *